(12) United States Patent
Sinkus et al.

(10) Patent No.: US 8,347,692 B2
(45) Date of Patent: Jan. 8, 2013

(54) METHOD FOR RHEOLOGICAL CHARACTERIZATION OF A VISCOELASTIC MEDIUM

(75) Inventors: Ralph Sinkus, Paris (FR); Michaël Tanter, Bagneux (FR); Mathias Fink, Meudon (FR); Jeremy Bercoff, Aix En Provence (FR); David Savery, Calas-Cabries (FR)

(73) Assignee: Super Sonic Imagine, Aix En Provence (FR)

( * ) Notice: Subject to any disclaimer, the term of this patent is extended or adjusted under 35 U.S.C. 154(b) by 335 days.

(21) Appl. No.: 12/666,240

(22) PCT Filed: Jun. 23, 2008

(86) PCT No.: PCT/FR2008/051129
§ 371 (c)(1),
(2), (4) Date: Dec. 22, 2009

(87) PCT Pub. No.: WO2009/007582
PCT Pub. Date: Jan. 15, 2009

(65) Prior Publication Data
US 2010/0170342 A1   Jul. 8, 2010

(30) Foreign Application Priority Data
Jun. 25, 2007   (FR) .................................... 07 04535

(51) Int. Cl.
*G01N 11/16* (2006.01)
*G01N 29/04* (2006.01)

(52) U.S. Cl. ........................................ 73/54.24; 73/579

(58) Field of Classification Search ................. 73/579, 73/54.28, 54.02, 54.24
See application file for complete search history.

(56) References Cited

U.S. PATENT DOCUMENTS

| 5,115,808 | A  | * | 5/1992 | Popovic et al. | 600/438 |
| 7,553,283 | B2 | * | 6/2009 | Sandrin et al. | 600/438 |
| 7,578,789 | B2 | * | 8/2009 | Sandrin et al. | 600/438 |
| 2006/0010964 | A1 | * | 1/2006 | Sparks et al. | 73/54.01 |
| 2007/0006651 | A1 |   | 1/2007 | Kruger et al. | |
| 2010/0160778 | A1 | * | 6/2010 | Eskandari et al. | 600/438 |

OTHER PUBLICATIONS

Thomas L. Szabo "The Domain Wave Equations for Lossy Media Obeying a Frequency Power Law";J. Accoust. Soc. Am., vol. 96, No. 1, Jul. 1994; pp. 491-500.

Shigao Chen, et al. "Quantifying Elasticity and Viscosity from Measurement of Shear Wave Speed Dispersion" J. Accoust, Soc. Am., vol. 115, No. 6, Jun. 2004; pp. 2781-2785.

(Continued)

*Primary Examiner* — Daniel Larkin
*Assistant Examiner* — Rose M Miller
(74) *Attorney, Agent, or Firm* — Miller, Matthias & Hull LLP

(57) ABSTRACT

Method for rheological characterization of a viscoelastic medium, with the following steps: (a) an excitation step during which a vibratory excitation is generated in the viscoelastic medium leading to a deformation of the medium, (b) a deformation measurement step during which the deformation of the medium caused by the excitation is observed, (c) and a characterization step during which at least one non-zero power parameter y is determined such that a rheological parameter of the medium x is equal to $x(f)=a+b \cdot f^y$, where f is the frequency, a is a real number and b a non-zero scale parameter. It is thus possible to obtain mapping of the power parameter y.

11 Claims, 3 Drawing Sheets

OTHER PUBLICATIONS

E.A. Barannik, et al. "The Influence of Viscosity on the Shear Strain Remotely Induced by Focused Ultrasound in Viscoelastic Media" J. Accoust.Soc. Am., vol. 115, No. 5, Pt. 1, May 2004; pp. 2358-2364.

Kendall R. Waters, et al. "On a Time-domain Representation of the Kramers-Krönig Dispersion Relations" J. Accoust. Soc. Am., vol. 106, No. 5, Pt. 1, Nov. 2000; pp. 2114-2119.

International Search Report from counterpart application No. PCT/FR08/51129; Report dated Jan. 20, 2009.

French Preliminary Search Report from French priority application FR 07 04535; Report dated Jan. 20, 2009.

Szabo Thomas L et al: "A model for longitudinal and shear wave propagation in viscoelastic media" *Journal of the Acoustical Society of America, AIP/Acoustical Society of America*, Melville, NY, US, vol. 107, No. 5, May 2000, pp. 2437-2446, XP012001666 ISSN: 0001-4966.

Robert B. et al. "A new rheological model based on fractional derivatives for biological tissues." IEEE Ultrasonics Symposium Oct. 3-6, 2006 1033-1036 XP002465566.

Chan Roger W et al. "Viscoelastic shear properties of human vocal fold mucosa: Measurement methodology and empirical results" Journal of the Acoustical Society of America, AIP/Acoustical Society of America, Melville, NY, US, vol. 106, No. 4, Oct. 1999 pp. 2008-2021 XP012001250: 0001-4966.

Bandyopadhyay et al. "Slow dynamics, aging, and glassy rheology in soft and living matter" Solid State Communications, Oxford, GB vol. 139, no Sep. 11-12, 2006 pp. 589-598 CP005615485: 0038-1098.

Kendall R. Waters, et al. "On the Applicability of Kramers-Krönig Relations for Ultrasonic Attenuation Obeying a Frequency Power Law" J. Accoust. Soc. Am., vol. 108, No. 2, Aug. 2000; pp. 556-563.

* cited by examiner

US 8,347,692 B2

METHOD FOR RHEOLOGICAL CHARACTERIZATION OF A VISCOELASTIC MEDIUM

CROSS-REFERENCE TO RELATED APPLICATIONS

This application is a U.S. national stage filing of International Patent Application No. PCT/FR2008/051129 filed on Jun. 23, 2008, which claims priority under the Paris Convention to French Application No. 0704535, filed on Jun. 25, 2007.

FIELD OF THE DISCLOSURE

The present invention relates to methods for rheological characterization of a viscoelastic medium.

BACKGROUND OF THE DISCLOSURE

More particularly, the invention relates to a method for rheological characterization of a viscoelastic medium, comprising the following steps:
  (a) an excitation step during which a vibratory excitation with a spectrum that includes at least one nonzero frequency is generated in the viscoelastic medium, said excitation producing a deformation of the medium;
  (b) a deformation measurement step during which said deformation of the medium produced by the excitation is observed at a plurality of points in the medium; and
  (c) a rheological characterization step during which at least one rheological parameter x of the medium is determined at said plurality of points in the medium from said deformation.

This thus allows qualitative and/or quantitative analysis, especially for identifying areas of different hardness from the rest of the viscoelastic medium or areas having a different relaxation time from the rest of the viscoelastic medium. One particularly advantageous application of this method is in the imaging of soft tissue in humans, for example for the purpose of detecting cancers.

Document WO-A-04/21038 describes an example of such a method.

Although this method has already given satisfaction, the object of the present invention is to further perfect methods of this type so as to improve the reliability and detection sensitivity thereof.

SUMMARY OF THE DISCLOSURE

For this purpose, a method of the kind in question is characterized in that, during the characterization step, a nonzero power parameter y is determined at said plurality of points in the medium, such that said rheological parameter of the medium is equal to: $x(f)=a+bf^y$, where f is said frequency, a is a real number and b is a nonzero scale parameter.

Thus, it is possible to characterize the viscoelastic medium in a very pertinent manner, enabling for example certain singular points in the medium, such as especially cancers in living tissue, to be detected more effectively.

In preferred embodiments of the method according to the invention, one or more of the following arrangements may optionally be furthermore employed:
  during the characterization step, the scale parameter b is also determined at said plurality of points in the medium;
  said rheological parameter x is an attenuation coefficient of the mechanical waves in the medium;
  said rheological parameter x is a coefficient of propagation of the mechanical waves in the medium;
  said excitation generates a shear wave in the medium;
  said rheological parameter is the real part of the complex shear modulus G* of the medium;
  said rheological parameter is the imaginary part of the complex shear modulus G* of the medium;
  said excitation is generated locally by a mechanical vibrator that produces the shear wave from a point of contact between said vibrator and the medium;
  said shear wave is generated remotely by emitting, into the medium, ultrasonic compression waves suitable for locally displacing the medium;
  during the deformation measurement step (b), an image of the deformation produced by the excitation, in a region having at least two dimensions belonging to said medium, is formed;
  during the deformation measurement step (b), said deformation is measured by a method chosen from echography and MRI; and
  during the rheological characterization step (c), a map of the power parameter in the medium is determined.

Other features and advantages of the invention will become apparent over the course of the following description of one of its embodiments, given by way of nonlimiting example, in conjunction with the appended drawings.

DETAILED DESCRIPTION OF THE DISCLOSURE

In the various figures, the same references denote identical or similar elements.

The invention relates to a method for rheological characterization of a viscoelastic medium 1, for example soft tissue of a human organ, especially for the purpose of identifying anomalies such as cancers, from analysis of the rheological parameters in question.

Figure 1:
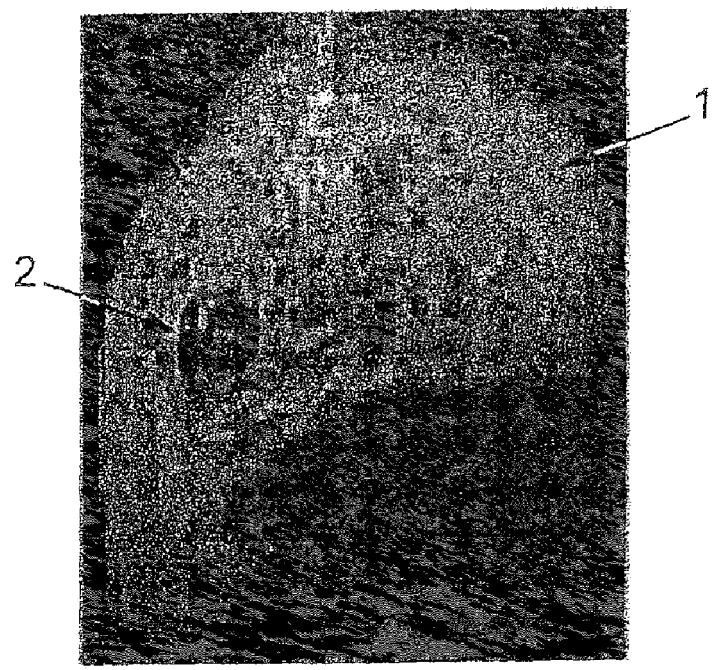
FIG. 1 is a two-dimensional MRI slice image of a breast of a patient suffering from an infiltrating canal carcinoma, in section in a sagittal plan.

To give an example, FIG. 1 shows an MRI slice image of a breast (constituting the abovementioned medium 1) of a patient suffering from an infiltrating canal carcinoma 2, corresponding to the area surrounded by a solid line in FIG. 1.

As may be seen in FIG. 1, the diseased part 2 of the medium 1 is not clearly distinguished from the healthy parts in the MRI slice image.

To improve the detection of anomalies such as a cancer or the like, it is therefore necessary to measure rheological parameters (at at least one point, or preferably over an entire region, in order to obtain a map of this rheological parameter) by means of a method of rheological characterization by elastography or the like, comprising the following steps:
  (a) an excitation step during which a vibratory excitation having a spectrum that includes at least one nonzero frequency f is generated in the viscoelastic medium 1, said excitation producing a deformation of the medium 1;

(b) a deformation measurement step during which said deformation of the medium 1 produced by the excitation is observed, at at least one point in the medium; and (c) a rheological characterization step during which at least one rheological parameter of the medium is determined at least at said point in the medium, from said deformation.

Such methods are known, in particular, from documents WO-A-2000/55616, WO-A-2004/021038 and WO-A-2006/010213.

The vibratory excitation may for example generate a shear wave in the medium:
either locally, by an external mechanical vibrator that produces the shear wave from the point of contact between said vibrator and the medium (as described for example in document WO-A-2000/55616), said vibrator therefore inducing an excitation, the spectrum of which may be a single-frequency spectrum or a broad spectrum, lying for example in a frequency band between 0 and 10 000 Hz;
or remotely by emitting, into the medium, ultrasonic compression waves suitable for locally displacing the medium (WO-A-2004/021038), these ultrasonic waves possibly having frequencies lying for example between 0.1 and 50 MHz, whether these be focused or not, which are created by an array of independent transducers or by a single-element transducer.

During the deformation measurement step (b), said deformation is measured by a method chosen in particular from echography and MRI, as illustrated for example in the abovementioned documents WO-A-2000/55616, WO-A-2004/021038 and WO-A-2006/010213.

During the deformation measurement step (b), an image of the deformation (deformation amplitude) produced by the excitation, in an at least two-dimensional region within the medium 1, is formed and, during the rheological characterization step (c), a map of the rheological parameter of the medium in said region may advantageously be determined.

The propagation of the mechanical waves (especially the abovementioned shear waves) in the medium 1 is modeled by the complex wavevector k which may be written as:

$$k(f) = \beta(f) + i\alpha(f) \tag{1}$$

where f is the frequency.

The imaginary part $\alpha$ of k represents the attenuation of the wave, while its real part $\beta$ represents the propagation: these parameters form part of the parameters characterizing the rheology of the medium 1.

According to the invention, at least one of the rheological parameters of the medium varies according to a power law of the frequency f. In other words, this parameter, which we will firstly call x, is an affine function of $f^y$ (f to the power y), where y is a nonzero real number that varies according to the location in the medium 1 (y is itself a parameter characterizing the rheology of the medium), namely: $x(f)=a+bf^y$, where a is a real number and b is a nonzero real number, called a scale parameter.

During the characterization step (c), at least the power parameter y and, as the case may be, the scale parameter b are determined.

According to this power law model, the attenuation a (expressed in nepers per cm) may for example be expressed as:

$$\alpha(f)=\alpha_1+\alpha_0 f^y \tag{2}$$

where $\alpha_1$ and $\alpha_0$ are two real numbers (according to the notation indicated above, in the general case: $x=\alpha(f)$; $a=\alpha_1$; and $b=\alpha_0$).

In general, the power y is between 0 and 2 for mechanical waves in biological tissue.

The causality rules, mathematically expressed by the Kramers-Kronig relations (see for example Szabo, J. Acoust. Soc. Amer. 107(5), part 1, May 2000, pp. 2437-2446 and Szabo, J. Acoust. Soc. Amer. 96(1), July 1994, pp. 491-500), impose a relationship between $\alpha$ and $\beta$ which physically amounts to quantifying the dispersion of the propagation velocity of the mechanical wave. For an attenuation verifying the above equation, $\beta$ must be expressed (see in particular Waters et al., J. Acoust. Soc. Amer. 108(2), August 2000, pp 556-563 and Waters et al., J. Acoust. Soc. Amer. 108(5), part 1, November 2000, pp 2114-2119):

for even or noninteger y, as:

$$\beta(f) = \beta(f_0) + \alpha_0 \tan\left(\frac{\pi y}{2}\right)(f^y - f_0^y) \tag{3}$$

and for odd y, as:

$$\beta(f) = \beta(f_0) - \frac{2}{\pi}\alpha_0 f^y (\ln(f) - \ln(f_0)) \tag{4}$$

$f_0$ being a reference frequency.

More generally, the power law may relate to any one of the following rheological parameters x:
the attenuation: $\alpha(f)=\alpha_1+\alpha_n f^y$, as indicated above; and/or
the propagation: $\beta(f)=\beta_1+\beta_0 f^y$, where $\beta_1$ and $\beta_0$ are two real numbers (according to the notation indicated above, in the general case: $x=\beta(f)$; $a=\beta_1$; and $b=\beta_0$); and/or
the real part and/or the imaginary part of the complex modulus $G^*$ (one or both parts thus being an affine function of $f^y$),
which constitute as many usable rheological parameters, in addition to the power y itself, and the map of which in the investigated region of the medium 1 is established during the abovementioned step (c).

The spatial variations in the rheological parameter or parameters adopted may be estimated by analyzing the spatio-temporal response of the medium to the mechanical excitation over the entire imaged area, and in particular:
by analyzing the complex modulus $G^*$ of the induced displacement field over the entire imaged area; or
by analyzing the group velocity and the attenuation of the wave produced by the excitation over the entire imaged area.

To give an example, in the case of investigation of the breast 1 shown in FIG. 1, shear waves are propagated in the breast 1, the propagation of said waves being observed by MRI by measuring the displacements u of the medium 1, and then a rheological model is used which is based on a power law for the attenuation of the shear waves:

$$\alpha(f)=\alpha_1+\alpha_0 f^y \tag{2}$$

The causality determines the frequency behavior of the real part of the wave vector, i.e. the propagation coefficient:

for $y>0$, $y>2$ and $y\neq 1$, $$\beta(f) = \beta(f_0) + \alpha_0 \tan\left(\frac{\pi y}{2}\right)(f^y - f_0^y). \tag{3}$$

Assuming that $\beta$ is zero at zero frequency and $\alpha_1$ is negligible, it follows that:

$$\beta \approx \tan\left(\frac{\pi}{2}y\right)\alpha_0 \omega^y = \chi\alpha_0\omega^y. \tag{5}$$

From this, the following is obtained:

$$k^2 = \beta^2 - \alpha^2 + 2i\alpha\beta = \alpha_0^2 \omega^{2y}(\chi^2 - 1 + 2i\chi) = Ae^{i\phi} \quad (6)$$

where $A = \alpha_0^2 \omega^{2y} \sqrt{(\chi^2-1)^2 + (2\chi)^2}$ and $$\tan(\varphi) = -\frac{2\chi}{1-\chi^2} = -\tan(\pi y)$$

where $\phi = -\pi y$.

We therefore obtain the expression for the complex shear modulus G* as:

$$G^* = \frac{\rho \omega^2}{\alpha_0^2 \omega^{2y} \sqrt{(\chi^2-1)^2 + (2\chi)^2}} e^{i\pi y} \quad (7)$$

i.e.:

$$G^* = \frac{\rho}{\alpha_0^2 \sqrt{(\chi^2-1)^2 + (2\chi)^2}} \omega^{2-2y}[\cos(\pi y) + i\sin(\pi y)]. \quad (8)$$

The ratio of the real part to the imaginary part of the complex shear modulus is then directly related to the power law y:

$$\frac{G_I}{G_d} = \tan(\pi y) \text{ and} \quad (9)$$

$$G_d \propto G_I \propto \varpi^{2-2y}. \quad (10)$$

When y tends toward 0, the material is a purely elastic solid, whereas the closer y approaches 0.5, the closer the medium approaches the behavior of a purely viscous liquid.

In the example in question, a monochromatic external vibration (i.e. a vibration having a single vibration frequency) was applied to the patient's breast 1 by a mechanical vibrator. The displacement field u was measured by MRI and the complex shear modulus G* was deduced from these measurements:

$$G^*(\omega) = \rho \frac{\omega^2 \text{rot}(u)}{\Delta(\text{rot}(u))}. \quad (11)$$

This experiment is repeated for several frequencies within the 65-100 Hz range so as to study the frequency dependency of the modulus. The results show unambiguously a dependence of the real part $G_d$ and the imaginary part $G_1$ of the modulus with the frequency f according to a power law. The frequency dependency of $G_1$ and the frequency dependency of $G_d$ are experimentally identical, as predicted by the model in question. The power law of G* is estimated to be γ=2-2y=1.67±0.24, which corresponds to y=0.165.

It should be noted that y may be estimated directly by evaluating the value of $G_1/G_d$ at a single frequency. Using this method, γ is estimated to be equal to 1.74±0.07, which corresponds quite well to the multi-frequency estimation.

This implies, under the abovementioned hypotheses, that a local estimate of $\alpha_0$ or $\beta_0$ and of the power law y may be envisioned at a single frequency.

Figure 2:
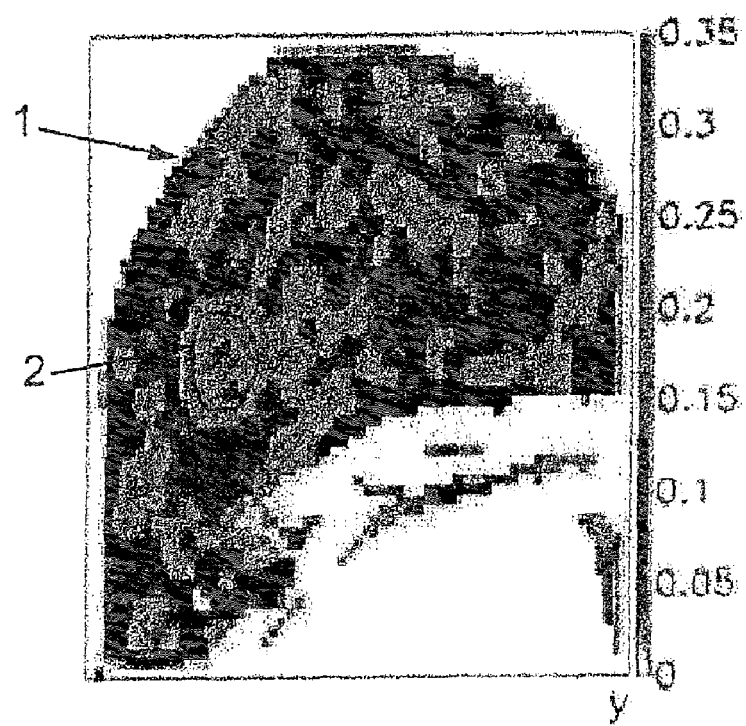
FIG. 2 shows a map of the power parameter y in the breast at a single frequency.
Figure 3:
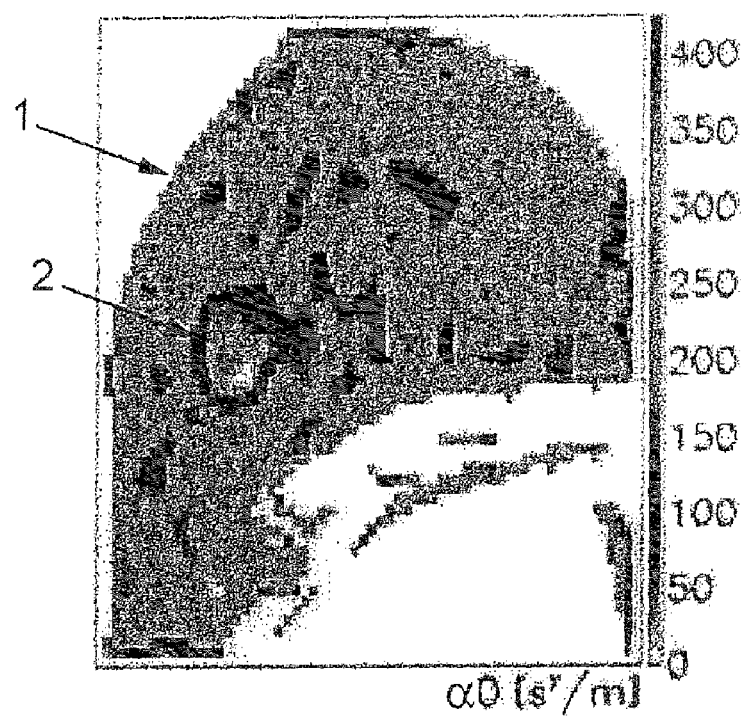
FIG. 3 shows a map of the local estimate $\alpha_o$ in the breast at a single frequency.

FIGS. 2 and 3 show such maps of y and $\alpha_0$, which are obtained with a monochromatic excitation of 80 Hz frequency. These two maps make it possible to locate, with great precision and both high contrast, the infiltrating canal carcinoma from which the patient is suffering.

Similar results may be obtained with y and $\beta_0$.

Figure 4:
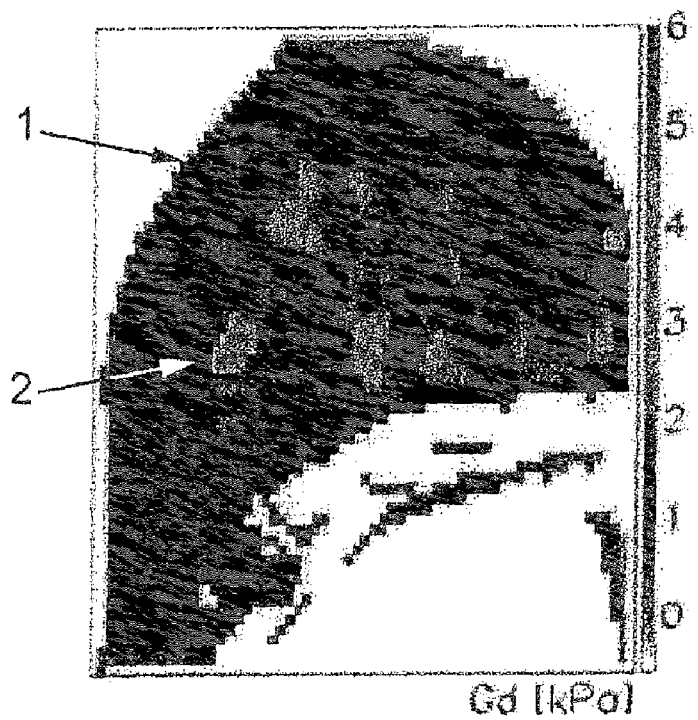
FIG. 4 shows a map of $G_d$ in the breast at a single frequency.
Figure 5:
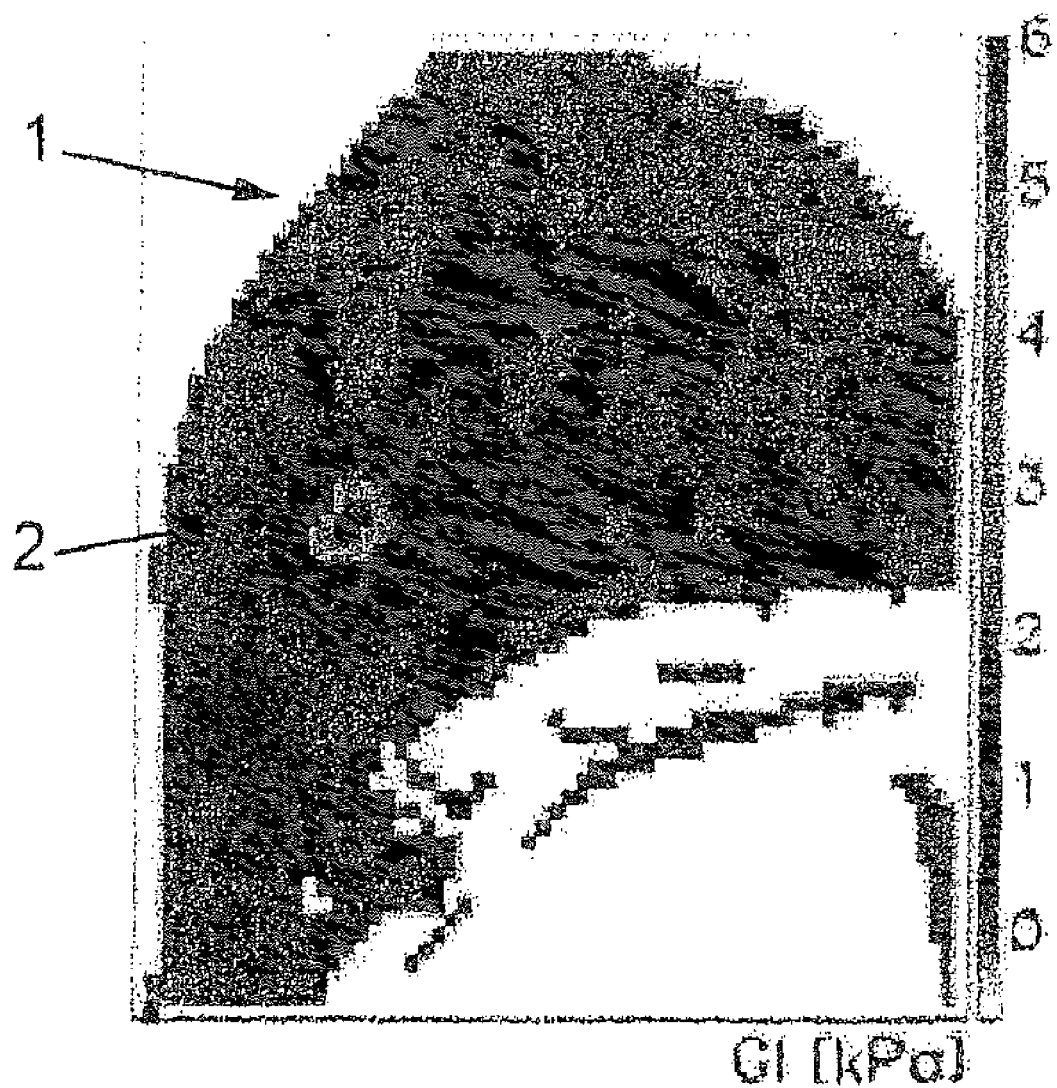
FIG. 5 shows a map of $G_1$ in the breast at a single frequency.

The $G_d$ and $G_1$ maps, obtained under the same conditions, are shown in FIGS. 4 and 5.

The invention claimed is:

1. A method for rheological characterization of a viscoelastic medium, comprising the following steps:
    (a) an excitation step during which a vibratory excitation with a spectrum that includes at least one nonzero frequency is generated in the viscoelastic medium, said excitation producing a deformation of the medium;
    (b) a deformation measurement step during which said deformation of the medium produced by the excitation is observed at a plurality of points in the medium; and
    (c) a rheological characterization step during which at least one rheological parameter x of the medium is determined at said plurality of points in the medium from said deformation,
    wherein, during the characterization step, a nonzero power parameter y is determined at said plurality of points in the medium, such that said rheological parameter of the medium is equal to: x(f)=a+bf$^y$, where f is said frequency, a is a real number and b is a nonzero scale parameter and a map of the power parameter in the medium is determined.

2. The method as claimed in claim 1, in which, during the characterization step, the scale parameter b is also determined at said plurality of points in the medium.

3. The method as claimed in claim 1, in which said rheological parameter x is an attenuation coefficient of the mechanical waves in the medium.

4. The method as claimed in claim 1, in which said rheological parameter x is a coefficient of propagation of the mechanical waves in the medium.

5. The method as claimed in claim 1, in which said excitation generates a shear wave in the medium.

6. The method as claimed in claim 5, in which said rheological parameter x is the real part of the complex shear modulus G* of the medium.

7. The method as claimed in claim 5, in which said rheological parameter x is the imaginary part of the complex shear modulus G* of the medium.

8. The method as claimed in claim 5, in which said excitation is generated locally by a mechanical vibrator that produces the shear wave from a point of contact between said vibrator and the medium.

9. The method as claimed in claim 5, in which said shear wave is generated remotely by emitting, into the medium, ultrasonic compression waves suitable for locally displacing the medium.

10. The method as claimed in claim 1, in which, during the deformation measurement step, an image of the deformation produced by the excitation, in a region having at least two dimensions belonging to said medium, is formed.

11. The method as claimed in claim 1, in which, during the deformation measurement step, said deformation is measured by a method chosen from echography and MRI.

* * * * *